(12) United States Patent
Castle

(10) Patent No.: US 11,918,538 B1
(45) Date of Patent: Mar. 5, 2024

(54) SYSTEM AND METHOD FOR VISION TRAINING USING SPECIALIZED GOGGLES

(71) Applicant: Christopher J. Castle, Columbus, OH (US)

(72) Inventor: Christopher J. Castle, Columbus, OH (US)

( * ) Notice: Subject to any disclaimer, the term of this patent is extended or adjusted under 35 U.S.C. 154(b) by 681 days.

(21) Appl. No.: 17/086,566

(22) Filed: Nov. 2, 2020

Related U.S. Application Data

(60) Provisional application No. 62/934,062, filed on Nov. 12, 2019.

(51) Int. Cl.
| A61H 5/00 | (2006.01) |
| A61F 9/02 | (2006.01) |
| A61F 9/04 | (2006.01) |
| A63B 69/00 | (2006.01) |
| G09B 17/04 | (2006.01) |

(52) U.S. Cl.
CPC ............... *A61H 5/00* (2013.01); *A61F 9/029* (2013.01); *A61F 9/04* (2013.01); *A63B 69/0055* (2020.08); *G09B 17/04* (2013.01)

(58) Field of Classification Search
CPC ... A61H 5/00; A61F 9/029; A61F 9/04; A63B 69/0055; G09B 17/04
USPC .......................................................... 351/203
See application file for complete search history.

(56) References Cited

U.S. PATENT DOCUMENTS

| 2007/0285797 | A1* | 12/2007 | Osetinsky | G02B 27/288 |
| | | | | 359/639 |
| 2008/0055541 | A1* | 3/2008 | Coulter | G02C 7/101 |
| | | | | 351/159.45 |
| 2011/0242480 | A1* | 10/2011 | Reichow | G02C 5/146 |
| | | | | 351/159.6 |
| 2015/0185503 | A1* | 7/2015 | Tate | G02C 7/083 |
| | | | | 351/159.01 |
| 2020/0122015 | A1* | 4/2020 | Mast | A63B 71/0622 |

* cited by examiner

*Primary Examiner* — Mohammed A Hasan
(74) *Attorney, Agent, or Firm* — Ronald J Koch

(57) ABSTRACT

Specialized eyewear (e.g. goggles, or headpiece) are utilized that block or obscure all or a portion of a user's view in order to direct the user's attention on non-blocked or non-obscured areas for sports training.

4 Claims, 9 Drawing Sheets

FIG. 2 - Field of view of the human eye
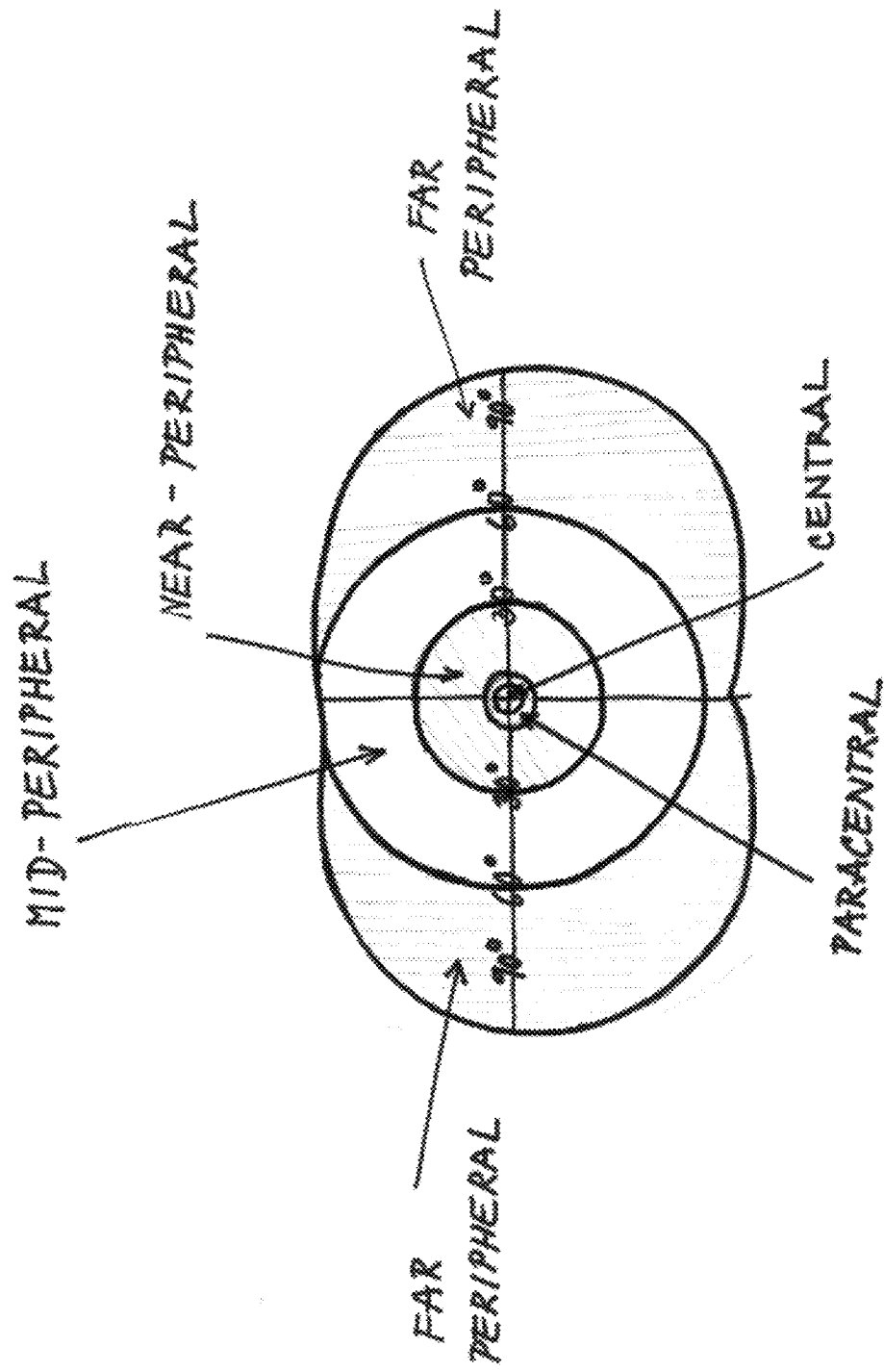

SYSTEM AND METHOD FOR VISION TRAINING USING SPECIALIZED GOGGLES

CROSS-REFERENCE TO RELATED APPLICATIONS

This application claims priority to U.S. provisional application No. 62/934,062, filed Nov. 12, 2019, the contents of which are hereby incorporated by reference.

FIELD

The present invention relates generally to systems and methods for athletic training, and more specifically to such systems and methods directed to selectively obscuring part of the field of vision to redirect focus to another part thereof.

BACKGROUND AND SUMMARY

Strong awareness of one's surroundings and fast reaction to relevant stimuli are critical skills for athletes, especially in field sports. Although an athlete's attention is generally focused on a particular object, such as an opposing player, or a ball, located in the athlete's central, or non-peripheral view, the athlete must be nevertheless able to react quickly to stimuli in the peripheral view. FIG. 2 depicts the user's field of view, and labels the various regions thereof.

Heretofore, existing systems and methods have been directed to helping athletes focus on the central field of view by blocking the athlete's peripheral view. FIGS. 1A & 1B depict such systems. FIG. 1A depicts goggles that block the far-peripheral side view. FIG. 1B depicts goggles that block the lower far-peripheral view. Such systems unfortunately do not help the athlete to react to stimuli outside of the central field of view. In fact, they accomplish the opposite, and thus teach away from the subject technology.

There is therefore a need for training systems and methods that help athletes react to stimuli outside of the central, or non-peripheral, field of view. Surprising and unexpected results are achieved by defying conventional thinking and using systems and methods that do the opposite of conventional systems; namely, selectively block or obscure all or portions of the non-far-peripheral view, thereby forcing the athlete to redirect focus to the parts of view that are not blocked or obscured.

In one aspect, specialized eyewear (e.g. goggles, or headpiece) are utilized that shield a portion of the view. In other aspects, such eyewear can be selectively adjustable to block varying ranges of view. In yet other aspects, such methods are practiced utilizing virtual or augmented reality. In one aspect, an accessory that fits over conventional sporting goggles is used. In some aspects, an entire portion of view is blocked (e.g. FIG. 3, 5A). In other aspects (e.g. FIGS. 4, 5B), a perforated light obstruction member (aka vision blocking shield) is used.

In some aspects, the subject technology comprises an implement worn on the head in the form of glasses, goggles, mask, or helmet. In one aspect, a headpiece is comprised of a frame and a vision blocking shield, with optional side support shields for supporting the vision blocking shield or as additional vision protection (e.g. FIGS. 3 & 4). In other aspects (FIGS. 5A & 5B), the subject technology is implemented using virtual reality (VR) and/or augmented reality (AR).

It should be understood that the subject technology has application in other areas in addition to sports training; such as medical, physical therapy, vision rehabilitation, eyesight education, reading training, and reading speed development and/or improvement.

BRIEF DESCRIPTION OF THE DRAWINGS

Further features of the inventive embodiments will become apparent to those skilled in the art to which the embodiments relate from reading the specification and claims with reference to the accompanying drawings, in which:

FIG. 2 depicts a graphical representation of the field of view of the human eye

REFERENCE NUMERALS IN DRAWINGS

Figure 1A:
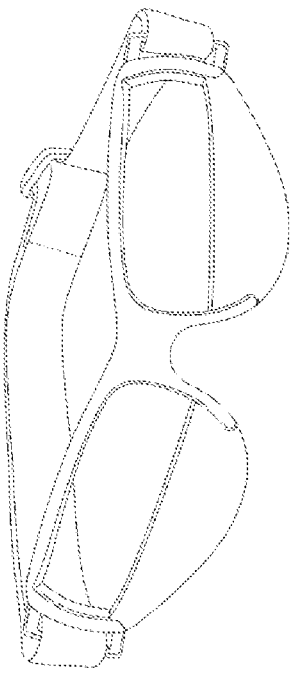
FIG. 1A depicts a prior art device
Figure 1B:
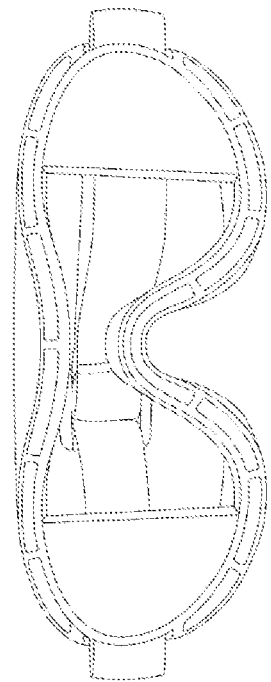
FIG. 1B depicts a prior art device

The table below lists the reference numerals employed in the figures, and identifies the element designated by each numeral.

1 headpiece 1
2 frame 2
4 vision blocking shield 4
6 support shield 6
8 shield carrier 8
10 perforated vision blocking shield 10
12 first virtual display (aka view) 12
14 second virtual display (aka view) 14
16 virtual vision blocking shield 16
18 virtual perforated vision blocking shield 18

DETAILED DESCRIPTION

FIG. 2 is a graphical representation of slightly over 180 degrees of the field of view of the human eyes, wherein the mid-peripheral view comprises a circular area from thirty to sixty degrees in both directions, inside of which the near peripheral view comprises a circular area in the range of zero to thirty degrees in both directions, with the central and paracentral views having concentric radii in the middle thereof; all of which being inside of the far-peripheral area. It is to be understood that these regions could be varied somewhat commensurate with varying user's and external stimuli, and topographies.

In one aspect of the subject technology, a vision training apparatus comprises a headpiece 1 comprising a frame 2 adapted to fit a user's head, and a light obstruction member 4 (e.g. vision blocking shield) operatively connected to the headpiece. In another aspect, the light obstruction member comprises a perforated light obstruction member 10.

Figure 3:
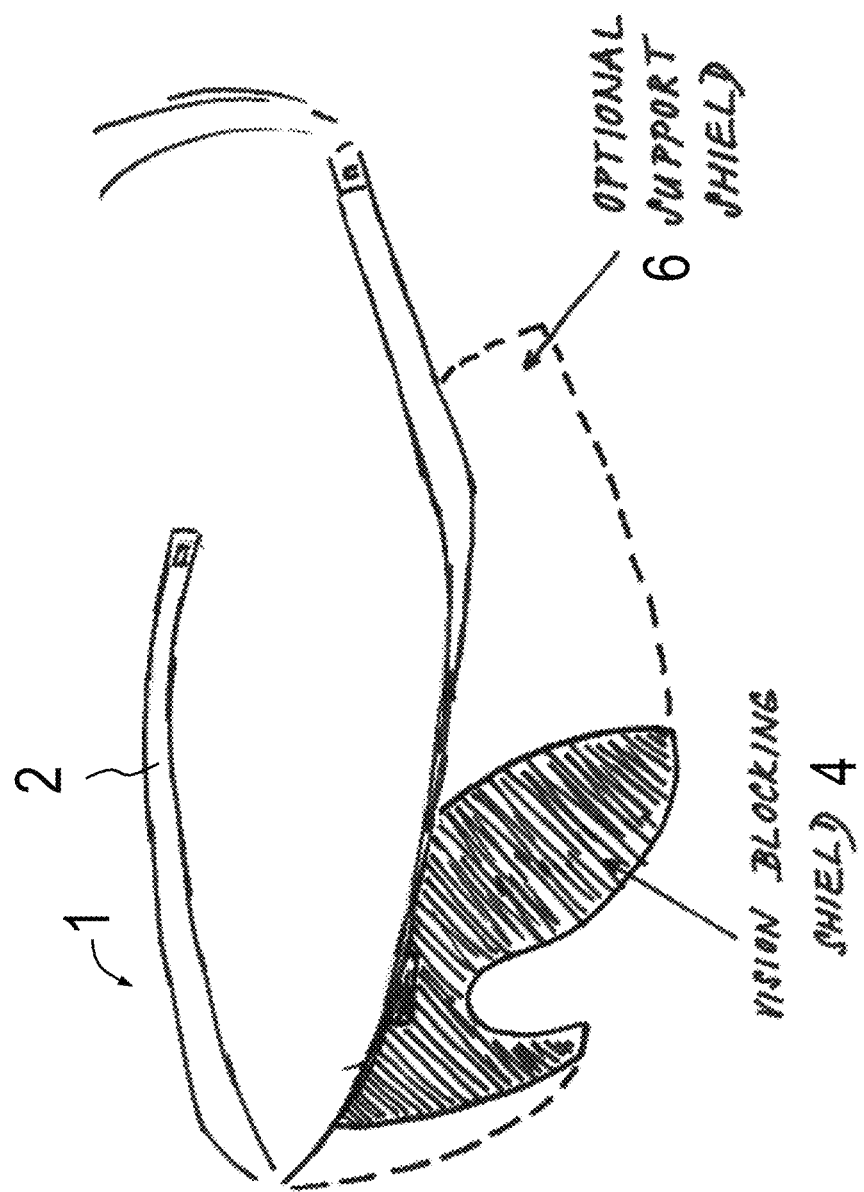
FIG. 3 depicts one aspect of the subject technology

As shown in FIG. 3, light obstruction member 4 (aka vision blocking shield) in one aspect is one piece formed so as to affect both eyes of a user. It should be noted that shield 4 can have different shapes and sizes. In another aspect (not shown), light obstruction member 4 is formed from two pieces instead of a unitary piece. Those of skill in the art will appreciate that the unitary piece can be separated without compromising the spirit of the invention. Additionally, a plurality of light obstruction members can be utilized and selectively arranged according to various objectives and teachings, including those herein. It should be understood that vision blocking shield 4 of FIG. 3 can alternatively be perforated, and likewise perforated vision blocking shield 10 of FIG. 4 can be non-perforated. In one aspect, light obstruction member 4 is connected directly to the frame 2. In another aspect, it is connected to support shield 6 which is connected to frame 2; said connectivity being achieved virtually, or by gluing, welding, integral fabrication, or molding.

Referring to FIG. 2, in one aspect, the light obstruction member 4 is adapted to block or obscure a portion of a user's central vision. In another aspect, a portion of a user's vision within a region from a mid-peripheral to a central region is blocked or obscured. It is to be understood that "within a region from a mid-peripheral to a central region" is defined to be a portion of a user's vision that can be anywhere from the mid-peripheral region, or inside of that region through the central region (e.g. the near-peripheral, paracentral, and central regions). In other words, a region excluding the far-peripheral region. However, in other aspects, the subject technology can be used to block or obscure at least a portion of the far-peripheral region, and in fact, any portion of a user's vision.

In other aspects, the light obstruction member(s) are sized and positioned so as to completely or partially block or obscure various areas of a user's vision, including the regions depicted in FIG. 2. This methodology can be practiced on one eye or both eyes, and the obstruction can be fully opaque, partially opaque, and/or perforated. The obstruction can be achieved physically (e.g. plastic) or via virtual or augmented reality. As a non-limiting example, the headpiece can be fitted with a transparent screen, which includes one or more layers that can be selectively controlled, for example, by utilizing an "active matrix" display having transparent transistors and/or circuits.

In one aspect, the light obstruction member is adapted to block or obscure a portion of a user's paracentral vision. In one aspect, the light obstruction member is adapted to block or obscure a portion of a user's near-peripheral vision. In one aspect, the light obstruction member is adapted to block or obscure a portion of a user's mid-peripheral vision.

Figure 6:
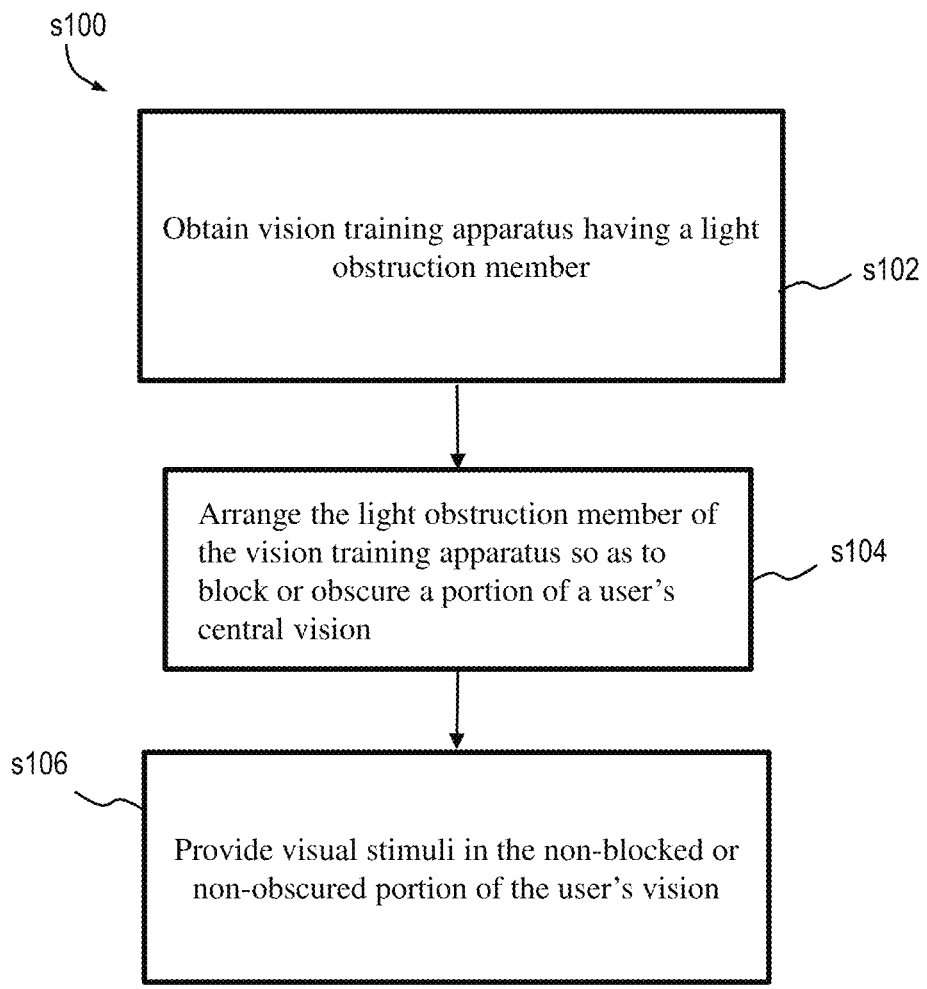
FIG. 6 depicts a flow chart describing one aspect of the subject technology

As shown in FIG. 6, in one aspect, a method s100 for vision training comprises the steps of: obtaining s102 a vision training apparatus comprising a headpiece 1 comprising a frame 2 adapted to fit a user's head, and a light obstruction member 4/10 operatively connected to the headpiece; and arranging s104 the light obstruction member so as to block or obscure a portion of a user's central vision. In one aspect, the method includes the step of providing s106 visual stimuli in the non-blocked or non-obscured portion of the user's vision.

Figure 7:
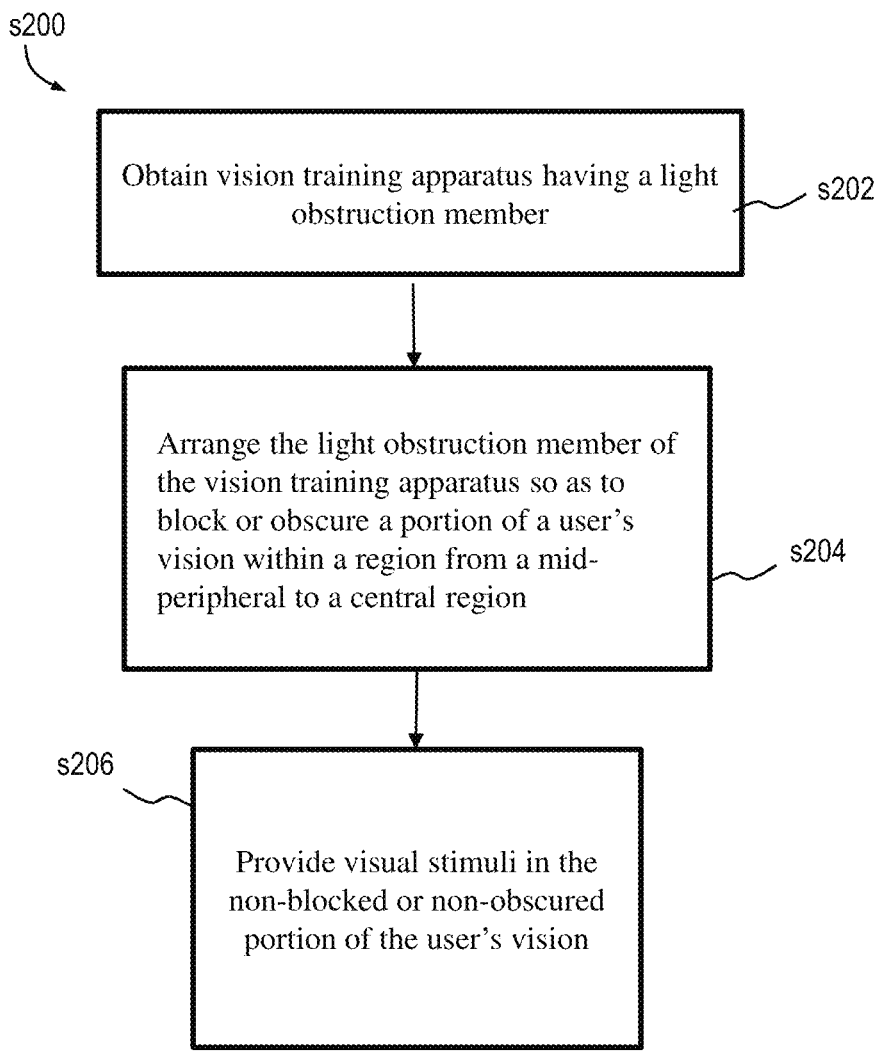
FIG. 7 depicts a flow chart describing one aspect of the subject technology

As shown in FIG. 7, in one aspect, a method s200 comprises the step s202 of obtaining a vision training apparatus comprising a headpiece 1 comprising a frame 2 adapted to fit a user's head, and a light obstruction member 4/10 operatively connected to the headpiece, then arranging s204 the light obstruction member so as to block or obscure a portion of a user's vision within a region from a mid-peripheral to a central region. In one aspect, the method includes the step of providing s206 visual stimuli in the non-blocked or non-obscured portion of the user's vision.

Figure 4:
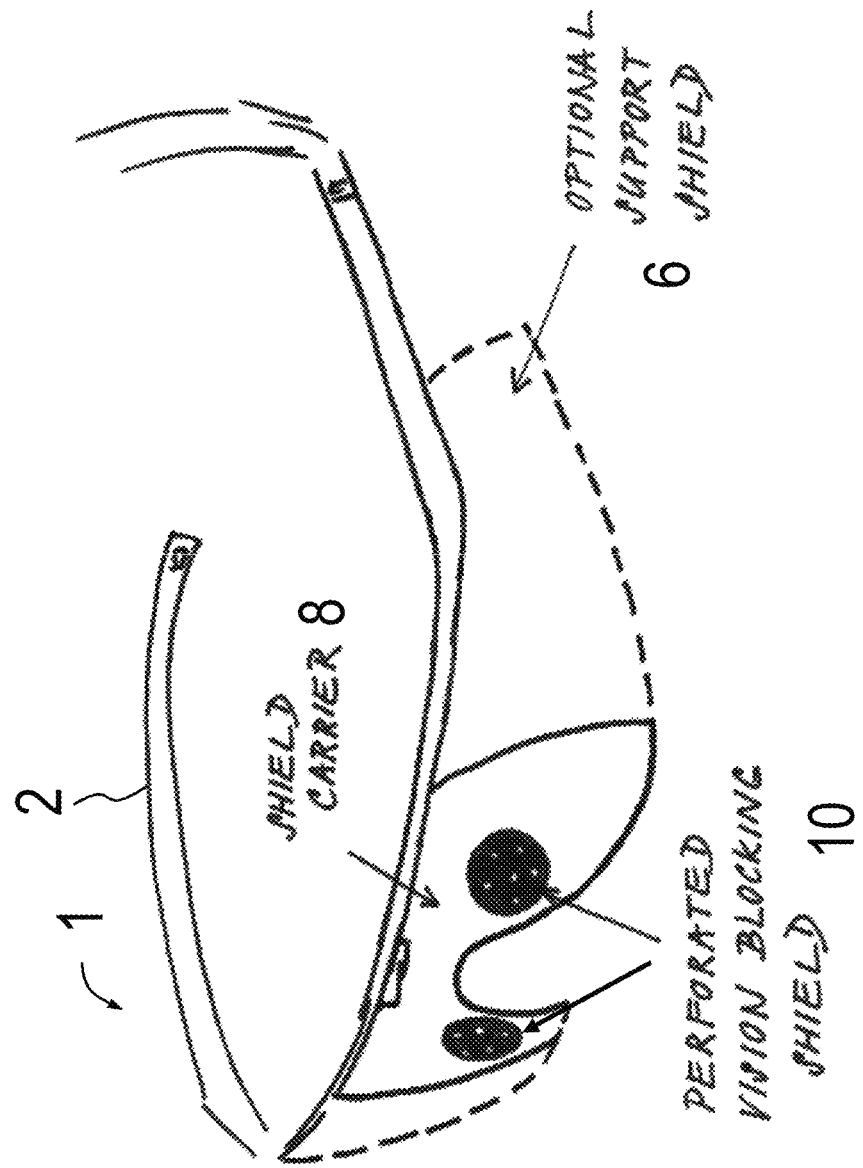
FIG. 4 depicts one aspect of the subject technology

In one aspect (e.g. FIG. 4), a plurality of light obstruction members 10 are operatively connected to the headpiece 1. As shown in FIG. 4, perforated light obstruction members 10 are connected to a shield carrier 8, which is connected to the frame 2; in another aspect, shield carrier 8 is connected to support shield 6, which is connected to the frame 2; said connectivity being achieved virtually, or by gluing, welding, integral fabrication, or molding. In one aspect, one or more of the plurality of light obstruction members is adapted to block or obscure a portion of a user's central vision. In one aspect, one or more of the plurality of light obstruction members is adapted to block or obscure a portion of a user's vision within a region from a mid-peripheral to a central region.

Figure 8:
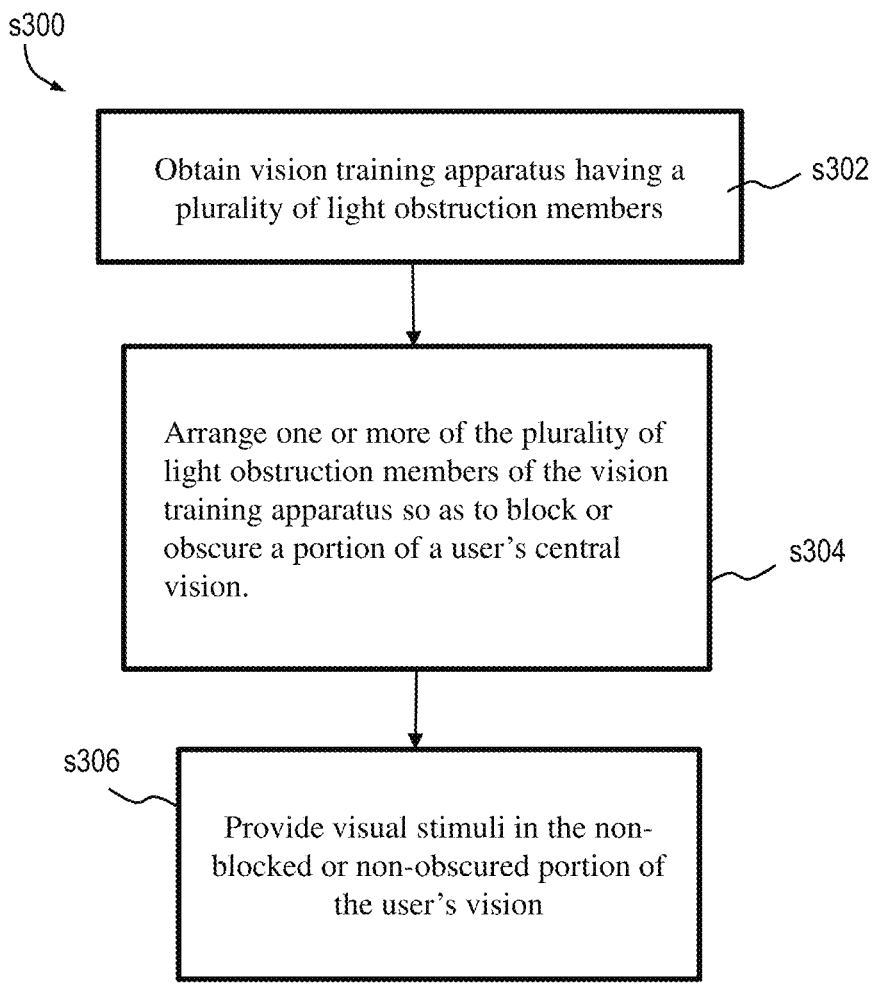
FIG. 8 depicts a flow chart describing one aspect of the subject technology

As shown in FIG. 8, in one aspect, a method s300 for vision training comprises the steps of: obtaining s302 a vision training apparatus comprising a headpiece 1 comprising a frame 2 adapted to fit a user's head, and a plurality of light obstruction members 4/10 operatively connected to the headpiece; and arranging s304 one or more of the plurality of light obstruction members so as to block or obscure a portion of a user's central vision. In one aspect, the method comprises the step of providing s306 visual stimuli in the non-blocked or non-obscured portion of a user's vision.

Figure 9:
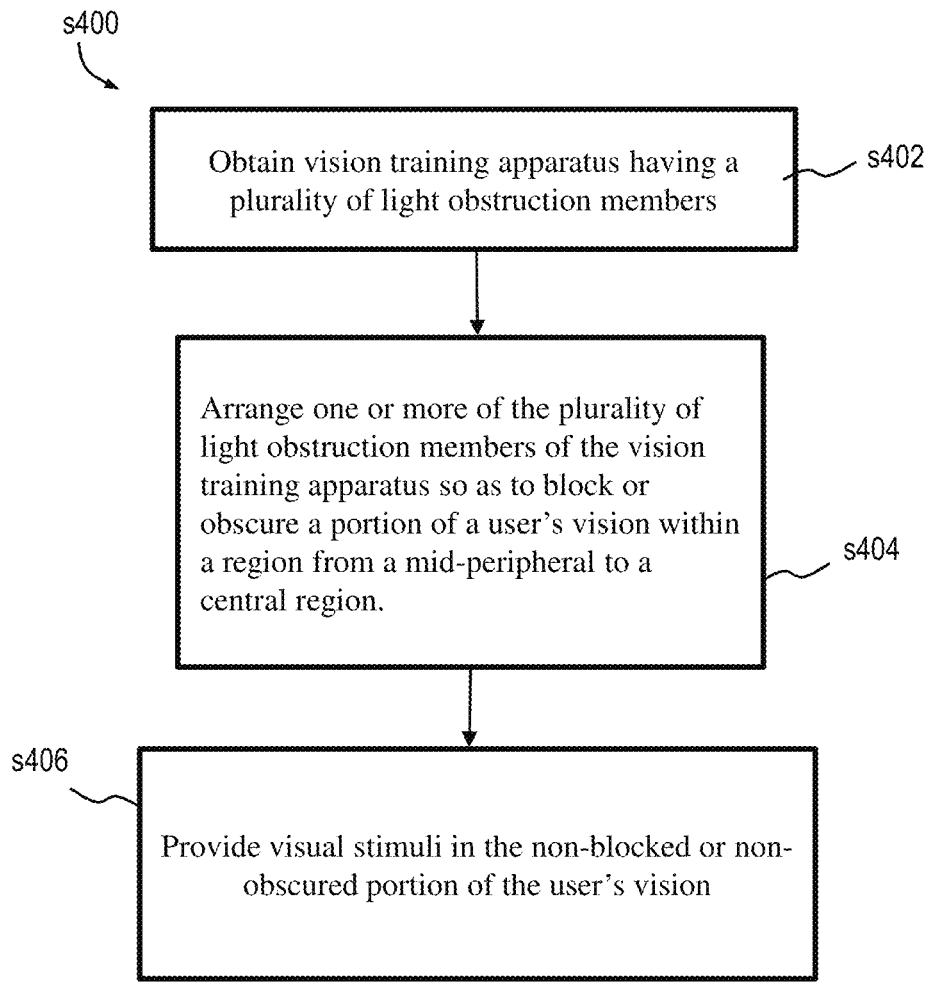
FIG. 9 depicts a flow chart describing one aspect of the subject technology

As shown in FIG. 9, in one aspect, a method s400 for vision training comprises the steps of: obtaining s402 a vision training apparatus comprising a headpiece 1 comprising a frame 2 adapted to fit a user's head, and a plurality of light obstruction members 4/10 operatively connected to the headpiece; and arranging s404 one or more of the plurality of light obstruction members so as to block or obscure a portion of a user's vision within a region from a mid-peripheral to a central region. In one aspect, the method comprises the step of providing s406 visual stimuli in the non-blocked or non-obscured portion of a user's vision. Whereby the foregoing methods allow a user wearing the vision training apparatus to react to visual stimuli in the non-blocked or non-obscured region of view in order to improve awareness of and reaction to such stimuli, and other training and benefits as will be apparent to those of skill in the art after having studied the subject technology.

In the various aspects described herein, the light obstruction member may comprise a perforated opaque or semi-opaque portion. As shown, for example in FIG. 4, the perforated portion allows some light to be transmitted therethrough, according to perforations that are selectively chosen according to varying perforation sizes and locations.

In one aspect, the light obstruction member is attached to the frame. In one aspect, the light obstruction member comprises a plurality of light obstruction members, such as for example, two such members, each of which may be disposed proximate a separate eye of a user. In one aspect (e.g. FIG. 3), the light obstruction member 4 is attached to a support shield 6 that is attached to the frame 2. In one aspect, the support shield is transparent (e.g. polycarbonate). In one aspect, the light obstruction member 10 is attached to a shield carrier 8 that is attached to the frame 2. In another aspect, the light obstruction member is attached to a shield carrier that is attached to the support shield.

Figure 5A:
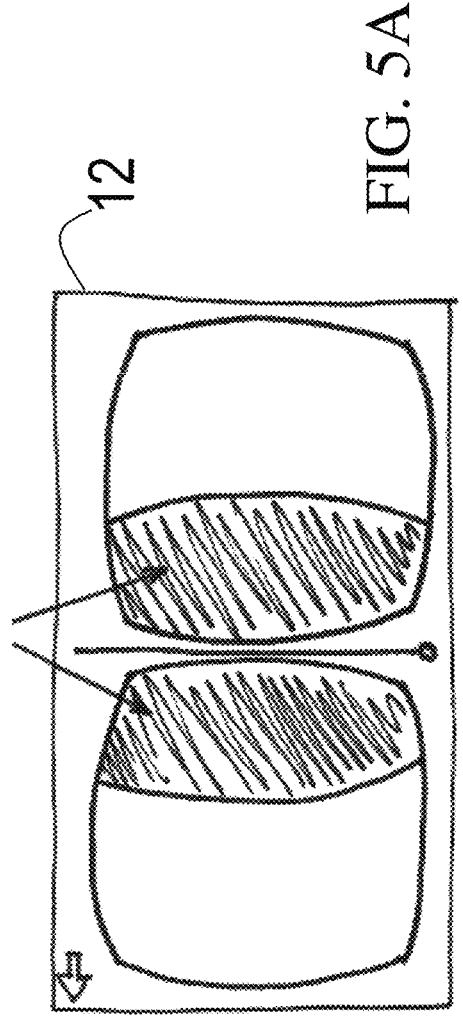
FIG. 5A depicts a graphical representation of virtual reality (VR)/augmented reality (AR) implementation
Figure 5B:
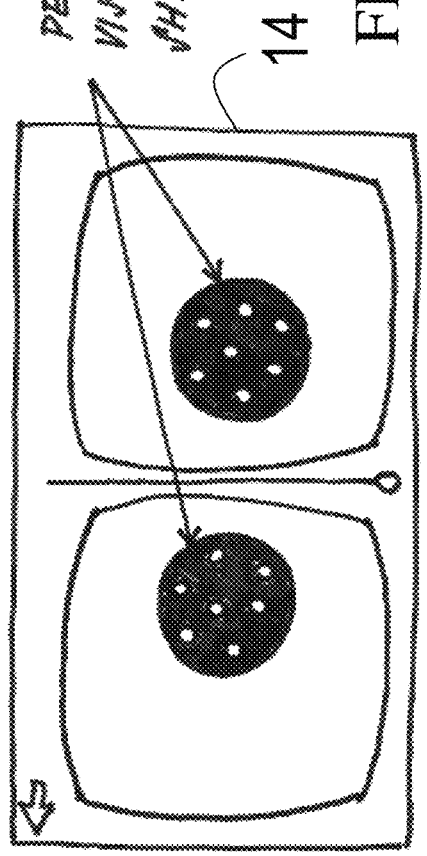
FIG. 5B depicts a graphical representation of virtual reality (VR)/augmented reality (AR) implementation

In one aspect (FIG. 3), a headpiece 1 comprises a frame 2 adapted to fit a user's head; and a vision blocking shield 4 attached to the frame 2, or alternatively to a support shield 6 attached to the frame 2. In one aspect, the support shield 6 is transparent (e.g. polycarbonate). In one aspect (FIG. 4), a shield carrier 8 is attached to the frame 2; and a perforated vision blocking shield 10 is attached to the shield carrier 8. In another aspect, the shield carrier 8 and vision blocking shield 10 are attached to support shield 6 which is attached to the frame 2. In one aspect (FIG. 5A), a first virtual display 12 comprises a virtual vision blocking shield 16. In one aspect (FIG. 5B), a second virtual display 14 comprises a virtual perforated vision blocking shield 18.

Turning now to FIG. 2, in one aspect, the subject technology is useful for improving reaction to stimuli coming from the areas of vision that are outside of a point of fixation (i.e. away from the center of gaze), mostly from the mid peripheral and far peripheral fields of view of the human eye. The theory of the subject technology is to fully or partially block or obscure an area of the vision in the non-peripheral field, or non-far-peripheral field, of vision (aka Focused Vision Area—FVA), while leaving the rest of the vision unobstructed, thereby forcing the mind to concentrate on the vision stimuli in the unobstructed area. It is to be understood that the various aspects of the subject technology as described herein can be varied to selectively block a range of views; thus, peripheral, or non-peripheral should not be strictly construed unless specifically claimed, and terms such as "peripheral", "non-peripheral", and "central" are used generally at times, but are also used specifically when referring to ranges such as those shown in FIG. 2. Unless specifically claimed, the terms "block", "obscure", and variations thereof, should not be strictly construed. For example, blocking a portion of a user's view could mean completely blocking (e.g. opaque object), or obscuring (e.g. using a semi-opaque, or perforated object).

In various aspects, VR/AR implementations may include training content, mimicking the features of physical implementations and may allow electronic configuration of the blocking shield. In some aspects, a transparent physical eyepiece comprises an electronic display having obscuring regions that can be dynamically and selectively varied. Such a physical eyepiece can be worn by the athlete while training in a non-virtual environment as well as a virtual environment, or a combination thereof.

In various aspects, physical implementations of vision blocking structures may be made of plastic, foil or other materials having suitable strength and opacity properties. In various aspects, full, partial, and perforated opacity characteristics are utilized. In some aspects, the width and shape of the blocking shield changes based on the stage of development of the athlete and the type of the desired training, ranging from small (covering a very narrow portion of the FVA), all the way to very wide (obstructing the field of vision into the far periphery).

It should be understood that the word "focus", as used within the context of the subject technology, can mean the focus of the eye (visual focus as achieved through the point of central fixation, through fovea centralis) and/or it can mean a directional concentration on something (i.e. the mind is focused on something, pays stronger attention to something).

The invention is in no way limited to the specifics of any particular embodiments and examples disclosed herein. For example, the terms "aspect," "example," "preferably," "alternatively," and the like denote features that may be preferable but not essential to include in some embodiments of the invention. In addition, details illustrated or disclosed with respect to any one aspect of the invention may be used with other aspects of the invention. Additional elements and/or steps may be added to various aspects of the invention and/or some disclosed elements and/or steps may be subtracted from various aspects of the invention without departing from the scope of the invention. Singular elements/steps imply plural elements/steps and vice versa. Some steps may be performed serially, in parallel, in a pipelined manner, or in different orders than disclosed herein. Many other variations are possible which remain within the content, scope, and spirit of the invention, and these variations would become clear to those skilled in the art after perusal of this application.

What is claimed is:

1. A vision training apparatus comprising:
a headpiece comprising a frame adapted to fit a user's head;
and a shield carrier operatively connected to the headpiece;
at least a portion of the shield carrier forming a vision blocking shield;
wherein the vision blocking shield continuously blocks the user's central vision.

2. A method for vision training comprising the steps of:
obtaining the apparatus of claim 1;
arranging the vision blocking shield so as to not block a portion of the user's peripheral vision.

3. The apparatus of claim 1 further comprising:
at least a portion of the shield carrier forming a plurality of vision blocking shields.

4. A method for vision training comprising the steps of:
obtaining the apparatus of claim 3;
arranging one or more of the plurality of vision blocking shields so as to not block a portion of the user's peripheral vision.

\* \* \* \* \*